United States Patent
Ernst et al.

(10) Patent No.: US 9,067,863 B2
(45) Date of Patent: *Jun. 30, 2015

(54) METHOD FOR PRODUCING AMINES FROM SUGAR ALCOHOLS

(75) Inventors: Martin Ernst, Heidelberg (DE); Bram Willem Hoffer, Fanwood, NJ (US); Johann-Peter Melder, Böhl-Iggelheim (DE)

(73) Assignee: BASF SE, Ludwigshafen (DE)

(*) Notice: Subject to any disclaimer, the term of this patent is extended or adjusted under 35 U.S.C. 154(b) by 763 days.

This patent is subject to a terminal disclaimer.

(21) Appl. No.: 12/675,423

(22) PCT Filed: Aug. 15, 2008

(86) PCT No.: PCT/EP2008/060742
§ 371 (c)(1),
(2), (4) Date: Feb. 26, 2010

(87) PCT Pub. No.: WO2009/027249
PCT Pub. Date: Mar. 5, 2009

(65) Prior Publication Data
US 2010/0311973 A1    Dec. 9, 2010

(30) Foreign Application Priority Data
Aug. 29, 2007 (EP) ..................... 07115219

(51) Int. Cl.
| | |
|---|---|
| C07C 209/00 | (2006.01) |
| C07C 209/16 | (2006.01) |
| C04B 24/12 | (2006.01) |
| C04B 28/02 | (2006.01) |
| C07C 213/02 | (2006.01) |
| C07D 241/04 | (2006.01) |
| C07D 295/02 | (2006.01) |
| C07D 295/023 | (2006.01) |

(52) U.S. Cl.
CPC ............. *C07C 209/16* (2013.01); *C04B 24/122* (2013.01); *C04B 28/02* (2013.01); *C07C 213/02* (2013.01); *C07D 241/04* (2013.01); *C07D 295/02* (2013.01); *C07D 295/023* (2013.01)

(58) Field of Classification Search
CPC .. C07C 209/16; C07C 213/02; C07C 211/09; C07C 211/10; C07C 211/11; C07C 215/08; C07D 241/04; C07D 295/02; C07D 295/023; C04B 24/122
USPC ........................... 564/479, 480; 544/358, 402
See application file for complete search history.

(56) References Cited

U.S. PATENT DOCUMENTS

| | | | |
|---|---|---|---|
| 2,004,135 A | 6/1935 | Rothrock | |
| 2,016,962 A | 10/1935 | Flint et al. | |
| 2,852,570 A | 9/1958 | Conradin et al. | |
| 4,843,154 A | 6/1989 | Klein et al. | |
| 5,091,369 A * | 2/1992 | Georgieff | 514/23 |
| 5,352,835 A * | 10/1994 | Dai et al. | 564/480 |
| 5,530,127 A | 6/1996 | Reif et al. | |
| 5,536,691 A | 7/1996 | Breitscheidel et al. | |
| 5,696,048 A | 12/1997 | Breitscheidel et al. | |
| 5,840,981 A | 11/1998 | Fuchs et al. | |
| 6,376,713 B1 * | 4/2002 | Baiker et al. | 564/479 |
| 6,525,222 B2 | 2/2003 | Nouwen et al. | |
| 6,821,396 B2 | 11/2004 | Wolfert et al. | |
| 6,916,964 B2 | 7/2005 | Gobbel et al. | |
| 7,618,917 B2 | 11/2009 | Vanoppen et al. | |
| 2004/0171889 A1 | 9/2004 | Vanoppen et al. | |
| 2009/0149314 A1 | 6/2009 | Ernst et al. | |

FOREIGN PATENT DOCUMENTS

| | | | |
|---|---|---|---|
| DE | 2445303 | | 4/1976 |
| EP | 0255033 | | 2/1988 |
| EP | 0356046 | * | 2/1990 |
| EP | 0636409 | | 2/1995 |
| EP | 0696572 | | 2/1996 |
| EP | 0742045 | | 11/1996 |
| EP | 0963975 | | 12/1999 |
| EP | 1106600 | | 6/2001 |
| EP | 1312600 | | 5/2003 |
| EP | 1318128 | | 6/2003 |
| EP | 1399255 | | 3/2004 |

(Continued)

OTHER PUBLICATIONS

Sheldon (Chirotechnology Industrial Synthesis of Optically Active Compounds 1993, downloaded from the internet on Jan. 22, 2014).*
Stiles, "Catalysts Prepared by Precipitation," *Catalyst Manufacture*, pp. 14-19, Marcel Dekker, Inc., New York, NY.
Stoehr, "Mittheilungen aus dem chemischen Institute der Uniersität Kiel," *Journal f prakt. Chemie*, vol. 2, No. 54, pp. 481-495.
Fischer, et al., "Amination of diols and polyols to acyclic amines," *Catalysis Today* (1997), vol. 37, pp. 167-189.

(Continued)

*Primary Examiner* — Yevegeny Valenrod
*Assistant Examiner* — Blaine G Doletski
(74) *Attorney, Agent, or Firm* — Drinker Biddle & Reath LLP

(57) ABSTRACT

The present invention relates to a process for preparing amines by reacting sugar alcohols with hydrogen and an aminating agent selected from the group of ammonia and primary and secondary amines in the presence of a catalyst at a temperature of from 100° C. to 400° C. and a pressure of from 1 to 40 MPa (from 10 to 400 bar). The catalyst preferably comprises one metal or a plurality of metals or one or more oxygen compounds of the metals of groups 8 and/or 9 and/or 10 and/or 11 of the Periodic Table of the Elements. The sugar alcohol is preferably obtained by hydrogenating the corresponding sugars. The invention further relates to the use of the reaction products as an additive in cement or concrete production and in other fields of use.

28 Claims, No Drawings

(56) References Cited

FOREIGN PATENT DOCUMENTS

| | | | |
|---|---|---|---|
| EP | 1412083 | | 4/2004 |
| FR | 2603276 | | 3/1988 |
| GB | 844448 | * | 8/1960 |
| GB | 1102370 | | 2/1968 |
| WO | WO-96/36589 | | 11/1996 |
| WO | WO-2005/051874 | | 6/2005 |
| WO | WO-2007/104663 | | 9/2007 |
| WO | WO2008/112952 | * | 9/2008 |
| WO | WO 2008/112952 | * | 9/2008 |

OTHER PUBLICATIONS

Jacobsen, et al., "Flame Hydrolysis," *Handbook of Heterogeneous Catalysis* (1997), pp. 94-100, VCH Verlagsgesellschaft mbH, D-69451 Weinheim, Germany.

Shu, "Degradation Products Formed from Glucosamine in Water," *J. Agric. Food Chem.* (1998), vol. 46, pp. 1129-1131.

Kelkenberg, "Detergenzien auf Zuckerbasis," *Tenside Surfactants Detergents* (1988), vol. 25, pp. 8-13.

Wainwright, "Skeletal Metal Catalysts," *Handbook of Heterogeneous Catalysis* (1997), pp. 64-72, VCH Verlagsgesellschaft mbH, D-69451 Weinheim, Germany.

Eller, et al., "Amines, Aliphatic," *Ullman's Encyclopedia* (2005), pp. 1-54, Wiley-VCH Verlag GmbH & Co. KGaA, Weinheim, Germany.

Frauenkron, et al., "Ethanolamines and Propanolamines," *Ullman's Encyclopedia* (2005), pp. 1-30, Wiley-VCH Verlag GmbH & Co. KGaA, Weinheim, Germany.

Sridhar, *Diamines and Higher Amines, Aliphatic*, vol. 8, pp. 485-519.

U.S. Appl. No. 12/675,413, filed Feb. 26, 2010, Ernst et al.

* cited by examiner

METHOD FOR PRODUCING AMINES FROM SUGAR ALCOHOLS

CROSS-REFERENCE TO RELATED APPLICATIONS

This application is a national stage application (under 35 U.S.C. §371) of PCT/EP2008/060742, filed Aug. 15, 2008, which claims benefit of European application 07115219.3, filed Aug. 29, 2007.

BACKGROUND OF THE INVENTION

The present invention relates to a process for preparing amines from sugar alcohols and to the use thereof.

The industrial scale preparation of industrially important aminoalkanols, such as ethanolamine and isopropanolamine, and their conversion products such as ethylenediamine, 1,2-propylenediamine and piperazine, generally proceeds from ethylene oxide or propylene oxide as a $C_2$ or $C_3$ synthesis unit.

For instance, ethanolamine and isopropanolamine are synthesized by reaction of ammonia with ethylene oxide and propylene oxide respectively. As further products, the corresponding dialkanolamines and trialkanolamines are also obtained in this reaction. The ratio of monoalkanolamines to di- and trialkanolamines can be controlled through the use amounts of ammonia relative to alkylene oxide. In order to obtain a higher proportion of trialkanolamines, mono- and dialkanolamines can be recycled into the reactor.

In a further reaction stage, the monoalkanolamines thus obtained can be converted further to ethylenediamine and 1,2-propylenediamine by reaction of hydrogen and ammonia.

1,3-Diaminopropane is obtainable on the industrial scale by reacting ammonia with acrylonitrile and subsequent hydrogenation, and acrylonitrile is generally prepared on the industrial scale by ammoxidizing the $C_3$ unit propene.

As an alternative raw material source to the ethene- or propene-based petrochemical feedstocks mentioned, raw materials based on renewable raw materials may achieve an ever higher status.

Sugar alcohols might gain growing significance in the future.

U.S. Pat. No. 2,016,962 describes the reaction of reducing sugars with hydrogen and an aminating agent (ammonia, primary or secondary amines) in the presence of hydrogenation catalysts (reduced nickel catalysts). The reaction should be performed preferably between 80 and 125° C., since monosaccharides such as glucose decompose in the course of heating. Glucamine and xylamine were obtained from glucose and xylose respectively.

Kelkenberg et al. (H. Kelkenberg, Tenside Surfactants Detergents, 25 (1988), pages 8-13) discloses the synthesis of glucamine by reaction of glucose with amine or ammonia to give the N-glucoside, which is subsequently hydrogenated to glucamine. The reaction is performed in an Ni fixed bed, but the exact reaction conditions are not specified. Excessively severe reaction conditions lead, according to the disclosure, to cleavage reactions and to the formation of ethylenediamine and ethanolamine.

EP-A2-0255033 describes the synthesis of isomaltines from disaccharides by catalytic reductive amination with hydrazine and hydrogen in the presence of Raney nickel catalysts. The reductive amination is performed at 50° C. and a pressure of from 100 to 150 bar.

EP-A2-03990488 likewise discloses the preparation of polyhydroxyamines from disaccharides by reductive amination with hydrazine and hydrogen in the presence of Raney nickel catalysts.

The review article by Fischer et al. (A. Fischer, T. Mallat, A. Baiker, Catalysis Today 37 (1997), pages 167-189) discusses the amination of sugars comprehensively. It is pointed out that the N-glucoside formed as an intermediate in the amination of glucose labile especially in the presence of water and tends to caramelization reactions (Maillard reactions). According to the disclosure, high hydrogenation rates are required in order to reduce the lifetime of the imine (N-glucoside) formed as an intermediate. It is also disclosed that, on the other hand, more severe hydrogenation conditions lead to cleavage products such as ethanolamine and diaminoethane.

BRIEF SUMMARY OF THE INVENTION

It was an object of the present invention to utilize sugar alcohols as a source for the preparation of amines. The intention was to provide a process which allows both important industrial amines and specialty amines, and also piperazine derivatives to be obtained, in order to be able to optimally utilize the raw material of sugar. Industrial amines refer to those amines which are typically obtained on the basis of petrochemical raw materials, for example monoamines such as methylamine, ethylamine, isopropylamine and n-propylamine, diamines such as ethylenediamine, 1,2-propanediamine and 1,3-propanediamine, alkanolamines such as monoethanolamine, 2-aminopropan-1-ol and 1-aminopropan-2-ol, or piperazine.

Specialty amines are amines which have at least three functional groups, at least one functional group being an amine function. Examples of such specialty amines are 1,2-diaminopropan-3-ol, isomaltine and glucosamine. Specialty amines derive structurally from sugar alcohols or cleavage products thereof.

These compounds have a high number of functionalities and may therefore be important intermediates in the synthesis of organic compounds, such as crop protection compositions, pharmaceuticals, stabilizers, etc.

Derivatives of piperazine (piperazine derivatives), such as 2-methylpiperazine or 2,6-dimethylpiperazine, may likewise be important synthesis units.

The conversion of sugar alcohols to the compounds mentioned should include only a few reaction steps in order to minimize the capital costs as far as possible.

By virtue of easy-to-perform adjustments to the process conditions, for example pressure and temperature, reaction time, catalyst hourly space velocity, variation of the molar aminating agent to sugar alcohol ratio, and also by virtue of selection of the catalyst used, it should additionally be possible to regulate the composition of the amine mixture within certain limits in order thus to be able to react better to demand and sales variations in relation to industrial amines, specialty amines or piperazine derivatives.

In addition, the formation of aromatic by-products, especially pyrazines and pyrazine derivatives, should be kept low, since they reduce the yield of industrial amines, specialty amines and piperazine derivatives. The formation of such heteroaromatic compounds from glucose is disclosed, for example, by Brandes et al. (P. Brandes, C. Stoehr, J. Prakt. Chem., 54 (1896), pages 481 to 495) or by Shu (C.-K. Shu, J. Agric. Food. Chem., 46 (1998), pages 1129 to 1131). As a result of the use of sugar alcohols instead of sugar itself, the formation of heteroaromatics is surprisingly suppressed.

According to the invention, a process has been found for preparing amines by reacting sugar alcohols with hydrogen and an aminating agent selected from the group of ammonia and primary and secondary amines in the presence of a catalyst at a temperature of from 100° C. to 400° C. and a pressure of from 1 to 40 MPa (from 10 to 400 bar).

DETAILED DESCRIPTION OF THE INVENTION

The conversion of sugar alcohols in the presence of hydrogen and of an aminating agent selected from the group of ammonia and primary and secondary amine is referred to hereinafter as hydrogenating amination of sugar alcohols or else only as hydrogenating amination for short.

The reactants used in the reaction are sugar alcohols, hydrogen and an aminating agent selected from the group consisting of ammonia and primary and secondary amines.

Examples of sugar alcohols are erythritol, threitol, ribitol, arabinitol, xylitol, lyxitol, allitol, altritol, glucitol (sorbitol), mannitol, gulitol, iditol, galactitol, talitol, ribulitol, xylulitol, psicitol, fructitol, tagatitol, isomaltitol (isomalt), lactitol, maltitol and lactulitol.

It is also possible to use mixtures of the abovementioned sugar alcohols in the process according to the invention.

In the process according to the invention, particular preference is given to using threitol, arabitol, erythritol, isomalt, lactitol, maltitol, mannitol, sorbitol and xylitol.

The sugar alcohols used in the process according to the invention are preferably obtained by reducing the aldehyde or carbonyl group of reducing sugars.

For instance, erythritol can be obtained by reducing erythrose, threitol by reducing threose, ribitol by reducing ribose, arabinitol by reducing arabinose, xylitol by reducing xylose, lyxitol by reducing lyxose, allitol by reducing allose, altritol by reducing altrose, glucitol (sorbitol) by reducing glucose, mannitol by reducing mannose, gulitol by reducing gulose, iditol by reducing idose, galactitol by reducing galactose, talitol by reducing talose, ribulitol by reducing ribulose, xylulitol by reducing xylulose, psicitol by reducing psicose, fructitol by reducing fructose, tagatitol by reducing tagatose, isomaltitol (isomalt) by reducing isomaltulose, lactitol by reducing lactose, maltitol by reducing maltose and lactulitol by reducing lactulose.

For instance, the aforementioned sugars are typically reduced with hydrogen at high pressures in the presence of hydrogenation catalysts, for example ruthenium, nickel or cobalt hydrogenation catalysts.

Processes for preparing xylitol, sorbitol, mannitol, isomalt, lactitol, maltitol and erythritol are described, for example, in Ullmann (Ullmann's Encyclopedia of Industrial Chemistry, "Sugar Alcohols", Wiley-VCH-Verlag, Electronic Edition, 2007).

Preference is given to preparing sugar alcohols, especially sorbitol, by the process described in EP-A-1412083 (BASF Aktiengesellschaft) or EP-A-1399255 (BASF Aktiengesellschaft) by reducing glucose with hydrogen over Ru catalysts.

As a further feedstock, hydrogen is used in the process.

The aminating agent is selected from the group consisting of ammonia, primary amine and secondary amine.

As well as ammonia, it is equally possible to use primary or secondary amines as aminating agents.

For example, the following mono- and dialkylamines may be used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentyl-amine, isopentylamine, n-hexylamine, s-hexylamine, isohexylamine, cyclohexylamine, aniline, toluidine, piperidine, morpholine and pyrrolidine.

However, preference is given to using inexpensive aminating agents available on the industrial scale, such as ammonia, methylamine or diethylamine.

Particular preference is given to using ammonia as the aminating agent.

The catalysts used in the process according to the invention comprise one or more metals of groups 8 and/or 9 and/or 10 and/or 11 of the Periodic Table of the Elements (Periodic Table in the IUPAC version of Jun. 22, 2007, http://www.iupac.org/reports/periodic_table/IUPAC_Periodic_Table-22Jun07b.pdf). Examples of such metals are Cu, Co, Ni and/or Fe, and also noble metals such as Rh, Ir, Ru, Pt, Pd, and Re.

The abovementioned metals may be used in the form of metal meshes or grids.

In a preferred embodiment, the metals are used in the process according to the invention in the form of Raney sponge or skeletal catalysts. Particular preference is given to using Raney nickel and/or cobalt catalysts.

Raney nickel or cobalt catalysts are prepared typically by treating an aluminum-nickel or aluminum-cobalt alloy with concentrated sodium hydroxide solution, which leaches out the aluminum and forms a metallic nickel or cobalt sponge. The preparation of Raney catalysts is described, for example, in the Handbook of Heterogeneous Catalysis (M. S. Wainright in G. Ertl, H. Knözinger, J. Weitkamp (eds.), Handbook of Heterogeneous Catalysis, Vol. 1, Wiley-VCH, Weinheim, Germany 1997, page 64 ff.). Such catalysts are obtainable, for example, as Raney® catalysts from Grace or as Sponge Metal® catalysts from Johnson Matthey.

The catalysts usable in the process according to the invention may also be prepared by reducing so-called catalyst precursors.

The catalyst precursor comprises an active composition which comprises one or more catalytically active components and optionally a support material.

The catalytically active components are oxygen compounds of the metals of groups 8 and/or 9 and/or 10 and/or 11 of the Periodic Table of the Elements (Periodic Table in the IUPAC version of Jun. 22, 2007), for example their metal oxides or hydroxides (examples if appropriate), such as CoO, NiO, $Mn_3O_4$, CuO, $RuO(OH)_x$ and/or mixed oxides thereof, such as $LiCoO_2$.

The mass of the active composition is the sum of the mass of the support material and of the mass of the catalytically active components.

The catalyst precursors used in the process may, as well as the active composition, comprise shaping media such as graphite, stearic acid, phosphoric acid or further processing assistants.

The catalyst precursors used in the process may further comprise one or more doping elements (oxidation stage 0) or inorganic or organic compounds thereof, selected from groups 1 to 14 of the Periodic Table. Examples of such elements or compounds thereof are: transition metals such as Mn or manganese oxides, Re or rhenium oxides, Cr or chromium oxides, Mo or molybdenum oxides, W or tungsten oxides, Ta or tantalum oxides, Nb or niobium oxides or niobium oxalate, V or vanadium oxides or vanadyl pyrophosphate, zinc or zinc oxides, silver or silver oxides, lanthanides such as Ce or $CeO_2$ or Pr or $Pr_2O_3$, alkali metal oxides such as $K_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

In the process according to the invention, the catalyst precursors are preferably used in the form of catalyst precursors which consist only of catalytically active composition, if appropriate a shaping assistant (for example graphite or stearic acid) if the catalyst is used as a shaped body and if appropriate one or more doping elements, but do not comprise any further catalytically active accompanying substances in addition. In this connection, the support material is considered to form part of the catalytically active composition.

The compositions specified below relate to the composition of the catalyst precursor after its last heat treatment, which is generally a calcination, and before its reduction with hydrogen.

The proportion of the active composition based on the total mass of the catalyst precursor is typically 70% by weight or more, preferably from 80 to 100% by weight, more preferably from 90 to 99% by weight, especially from 92 to 98% by weight.

In a preferred embodiment, the active composition of the catalyst precursor does not comprise any support material.

The active composition of catalyst precursors which do not comprise any support material preferably comprises one or more active components selected from the group consisting of CoO, NiO, $Mn_3O_4$, CuO, $RuO(OH)_x$ and $LiCoO_2$.

More preferably, the active composition of catalyst precursors which do not comprise any support material comprises NiO and/or CoO.

Such catalyst precursors are, for example, catalysts disclosed in patent application PCT/EP2007/052013 which, before reduction with hydrogen, comprise a) cobalt and b) one or more elements of the alkali metal group, of the alkaline earth metal group, of the rare earth group or zinc or mixtures thereof, where elements a) and b) are present at least partly in the form of their mixed oxides, for example $LiCoO_2$, or catalysts disclosed in EP-A-0636409, whose catalytically active composition, before reduction with hydrogen, comprises from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.2 to 15% by weight of alkali metal, calculated as $M_2O$ (M=alkali metal), or catalysts disclosed in EP-A-0742045, whose catalytically active composition, before reduction with hydrogen, comprises from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.05 to 5% by weight of alkali metal, calculated as $M_2O$ (M=alkali metal).

In a further preferred embodiment, the active composition comprises—in addition to the catalytically active components—support material.

Catalyst precursors which comprise support material may comprise one or more catalytically active components, preferably CoO, NiO, $Mn_3O_4$, CuO and/or oxygen compounds of Rh, Ru and/or Ir.

The active composition of catalyst precursors which comprise support material more preferably comprises NiO and/or CoO.

The support materials used are preferably carbon such as graphite, carbon black and/or activated carbon, aluminum oxide (gamma, delta, theta, alpha, kappa, chi or mixtures thereof), silicon dioxide, zirconium dioxide, zeolites, aluminosilicates, etc., and mixtures of these support materials.

The proportion of support material in the active composition may vary over a wide range according to the preparation method selected.

In the case of catalyst precursors which are prepared by impregnation, the proportion of support material in the active composition is generally more than 50% by weight, preferably more than 75% by weight and more preferably more than 85% by weight.

In the case of catalyst precursors which are prepared by precipitation reactions such as coprecipitation or precipitative application, the proportion of support material in the active composition is generally in the range from 10 to 90% by weight, preferably in the range from 15 to 80% by weight and more preferably in the range from 20 to 70% by weight.

Such catalyst precursors which are obtained by precipitation reactions are, for example, catalysts disclosed in EP-A-696572, whose catalytically active composition, before reduction with hydrogen, comprises from 20 to 85% by weight of $ZrO_2$, from 1 to 30% by weight of oxygen compounds of copper, calculated as CuO, from 30 to 70% by weight of oxygen compounds of nickel, calculated as NiO, from 0.1 to 5% by weight of oxygen compounds of molybdenum, calculated as $MoO_3$, and from 0 to 10% by weight of oxygen compounds of aluminum and/or of manganese, calculated as $Al_2O_3$ and $MnO_2$ respectively, for example the catalyst disclosed in loc. cit, page 8, with the composition of 31.5% by weight of $ZrO_2$, 50% by weight of NiO, 17% by weight of CuO and 1.5% by weight of $MoO_3$, catalysts disclosed in EP-A-963 975, whose catalytically active composition, before reduction with hydrogen, comprises from 22 to 40% by weight of $ZrO_2$, from 1 to 30% by weight of oxygen compounds of copper, calculated as CuO, from 15 to 50% by weight of oxygen compounds of nickel, calculated as NiO, where the molar Ni:Cu ratio is greater than 1, from 15 to 50% by weight of oxygen compounds of cobalt, calculated as CoO, from 0 to 10% by weight of oxygen compounds of aluminum and/or of manganese, calculated as $Al_2O_3$ and $MnO_2$ respectively, and does not comprise any oxygen compounds of molybdenum, for example the catalyst A disclosed in loc. cit., page 17, with the composition of 33% by weight of Zr, calculated as $ZrO_2$, 28% by weight of Ni, calculated as NiO, 11% by weight of Cu, calculated as CuO, and 28% by weight of Co, calculated as CoO, copper catalysts disclosed in DE-A-2445303, for example the precipitated copper catalyst disclosed in example 1 there, which is prepared by treating a solution of copper nitrate and aluminum nitrate with sodium bicarbonate and subsequent washing, drying and heat treatment of the precipitate, and has a composition of approx. 53% by weight of CuO and approx. 47% by weight of $Al_2O_3$, or catalysts disclosed in WO 96/36589, especially those which comprise Ir, Ru and/or Rh and, as a support material, activated carbon.

The catalyst precursors may be prepared by known processes, for example by precipitation, precipitative application, impregnation.

In a preferred embodiment, catalyst precursors which are prepared by impregnation of support materials (impregnated catalyst precursors) are used in the process according to the invention.

The support materials which are used in the impregnation may, for example, be used in the form of powders or shaped bodies such as extrudates, tablets, spheres or rings. Support material suitable for fluidized bed reactors is preferably obtained by spray-drying.

Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary processes (A. B. Stiles, Catalyst Manufacture—Laboratory and Commercial Preparations, Marcel Dekker, New York, 1983), for example by application of a metal salt solution in one or more impregnation stages. Useful metal salts generally include water-soluble metal salts such as the nitrates, acetates or chlorides of the abovementioned elements. Thereafter, the impregnated support material is generally dried and, if appropriate, calcined.

The impregnation can also be effected by the so-called "incipient wetness method", in which the support material, according to its water absorption capacity, is moistened up to a maximum of saturation with the impregnation solution. The impregnation can, though, also be effected in supernatant solution.

In multistage impregnation processes, it is appropriate to dry between individual impregnation steps and, if appropriate, to calcine. Multistage impregnation should advantageously be employed when the support material is to be coated with metal salts in a relatively large amount.

To apply a plurality of metal components to the support material, the impregnation can be effected simultaneously with all metal salts or successively in any sequence of the individual metal salts.

In a further preferred embodiment, catalyst precursors are prepared by means of a combined precipitation (coprecipitation) of all of their components. To this end, a soluble metal salt of the corresponding metal oxides and if appropriate a soluble compound of a support material are generally admixed with a precipitant in a liquid under hot conditions and with stirring until the precipitation is complete.

The liquid used is generally water.

Useful soluble metal salts of the corresponding metal oxides typically include the corresponding nitrates, sulfates, acetates or chlorides of the metals of groups 8 and/or 9 and/or 10 and/or 11 of the Periodic Table of the Elements (Periodic Table in the IUPAC version of Jun. 22, 2007). Examples of such metals are Cu, Co, Ni and/or Fe, and also noble metals such as Rh, Ir, Ru, Pt, Pd, and Re.

The water-soluble compounds of a support material used are generally water-soluble compounds of Al, Zr, Si, etc., for example the water-soluble nitrates, sulfates, acetates or chlorides of these elements.

Catalyst precursors may also be prepared by precipitative application. Precipitative application is understood to mean a preparation method in which a sparingly soluble or insoluble support material is suspended in a liquid and then soluble metal salts of the corresponding metal oxides are added, which are then applied to the suspended support by adding a precipitant (for example described in EP-A2-1 106 600, page 4, and A. B. Stiles, Catalyst Manufacture, Marcel Dekker, Inc., 1983, page 15). Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

As soluble metal salts of the corresponding metal oxides come generally the corresponding nitrates, sulfates, acetates or chlorides of the metals of groups 8 and/or 9 and/or 10 and/or 11 of the Periodic Table of the Elements (Periodic Table in the IUPAC version of Jun. 22, 2007). Examples of such metals are Cu, Co, Ni and/or Fe, and also noble metals such as Rh, Ir, Ru, Pt, Pd and Re.

In the precipitation reactions, the type of soluble metal salts used is generally not critical. Since the principal factor in this procedure is the water solubility of the salts, one criterion is their good water solubility which is required for the preparation of these comparatively highly concentrated salt solutions. It is considered to be self-evident that, in the selection of the salts of the individual components, of course only salts with those anions which do not lead to disruption, whether by causing undesired precipitation reactions or by complicating or preventing precipitation by complex formation, are selected.

Typically, in the precipitation reactions, the soluble compounds are precipitated as sparingly soluble or insoluble, basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of from 20 to 100° C., particularly from 30 to 90° C., especially from 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left for a certain time after the precipitation, if appropriate under hot conditions or while passing air through them.

The precipitates obtained by these precipitation processes are typically processed by washing, drying, calcining and conditioning them.

After washing, the precipitates are dried generally at from 80 to 200° C., preferably from 100 to 150° C., and then calcined.

The calcination is performed generally at temperatures between 300 and 800° C., preferably from 400 to 600° C., especially at from 450 to 550° C.

After the calcination, the catalyst precursors obtained by precipitation reactions are typically conditioned.

The conditioning can, for example, be effected by adjusting the precipitated catalyst to a particular particle size by grinding.

After the grinding, the catalyst precursors obtained by precipitation reactions can be mixed with shaping assistants such as graphite or stearic acid and processed further to give shaped bodies.

Common shaping processes are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the literature references mentioned, the shaping process can afford shaped bodies in any three-dimensional shape, for example round, angular, elongated or the like, for example in the form of extrudates, tablets, granule, spheres, cylinders or grains. Common shaping processes are, for example, extrusion, tableting, i.e. mechanical pressing or pelletizing, i.e. compaction by circular and/or rotating motions. The conditioning or shaping is generally followed by a heat treatment. The temperatures in the heat treatment correspond typically to the temperatures in the calcination.

The catalyst precursors obtained by precipitation reactions comprise the catalytically active components in the form of a mixture of their oxygen compounds, i.e. especially as oxides, mixed oxides and/or hydroxides. The catalyst precursors thus prepared can be stored as such.

Before they are used as catalysts for the hydrogenating amination of sugar alcohols, catalyst precursors which have been obtained by impregnation or precipitation as described above are generally prereduced by treatment with hydrogen after the calcination or conditioning.

For prereduction, the catalyst precursors are generally first exposed to a nitrogen-hydrogen atmosphere at from 150 to 200° C. over a period of from 12 to 20 hours, and then treated in a hydrogen atmosphere at from 200 to 400° C. for another up to approx. 24 hours. This prereduction reduces some of the oxygen-metal compounds present in the catalyst precursors to the corresponding metals, such that they are present together with the different types of oxygen compounds in the active form of the catalyst.

In a preferred embodiment, the prereduction of the catalyst precursor is undertaken in the same reactor in which the hydrogenating amination of the sugar alcohols is subsequently performed.

The catalyst thus formed can, after the prereduction, be handled and stored under an inert gas such as nitrogen, or under an inert liquid, for example an alcohol, water or the product of the particular reaction for which the catalyst is used. The catalyst may, though, after the prereduction, also be passivated with an oxygen-comprising gas stream such as air or a mixture of air with nitrogen, i.e. be provided with a protective oxide layer.

The storage of the catalysts which have been obtained by prereduction of catalyst precursors under inert substances, or the passivation of the catalyst, enable uncomplicated and safe handling and storage of the catalyst. If appropriate, the catalyst must then be freed of the inert liquid before the start of the actual reaction, or the passivation layer must be removed, for example, by treatment with hydrogen or a hydrogen-comprising gas.

Before the start of the hydroamination, the catalyst can be freed of the inert liquid or passivation layer. This is done, for example, by treatment with hydrogen or a hydrogen-comprising gas. Preference is given to undertaking the hydroamination directly after the reduction of the catalyst precursor in the same reactor in which the reduction was also effected.

Catalyst precursors may, however, also be used in the process without prereduction, in which case they are then reduced by the hydrogen present in the reactor under the conditions of the hydrogenating amination, the catalyst generally being formed in situ.

In the process according to the invention, sugar alcohol is typically reductively aminated in the liquid phase, i.e. in molten form, or dissolved or suspended in a solvent or diluent.

Useful solvents or diluents include especially those which are capable of very substantially dissolving the reactant or mix completely with it and are inert under the process conditions.

Examples of suitable solvents and diluents are water and aliphatic alcohols, especially $C_{1-8}$-alcohols, particularly $C_{1-4}$-alcohols, such as methanol, ethanol, n- or isopropanol, n-, 2-, iso- or tert-butanol.

Particular preference is given to performing the reductive amination of sugar alcohols in the presence of water as a solvent or diluent.

The concentration of sugar alcohol in the liquid, solvent- or diluent-containing phase is preferably in the range from 10 to 80% by weight, more preferably from 30 to 70% by weight, based in each case on the total weight of the solution or suspension (without catalyst).

The process can be performed continuously, batchwise or semicontinuously. Preference is given to a continuous method, in which case the catalyst is preferably arranged as a fixed bed in the reactor.

It is also possible to perform the hydrogenating amination in a stirred autoclave, a bubble column, a circulation reactor, for example a jet loop, or a fixed bed reactor.

In the batchwise reductive amination, sugar alcohol is typically initially charged in the reactor as a melt, solution or suspension, preferably as solution, in a suitable solvent or diluent (see above); the catalyst material is generally suspended in the liquid phase. In order to ensure high conversion and high selectivity, the melt, solution or suspension of the sugar alcohol, and the catalyst and hydrogen gas, must generally be mixed well, for example by a turbine stirrer in an autoclave. The suspended catalyst material can be introduced and removed again with the aid of customary techniques (sedimentation, centrifugation, cake filtration, crossflow filtration). The catalyst can be used once or more than once. The catalyst concentration is advantageously from 0.1 to 20% by weight, preferably from 0.5 to 10% by weight, especially from 1 to 5% by weight, based in each case on the total weight of the solution or suspension (total weight with catalyst). The mean catalyst particle size is advantageously in the range from 0.001 to 1 mm, preferably in the range from 0.005 to 0.5 mm, especially from 0.01 to 0.25 mm.

In the continuous reductive amination, sugar alcohols are typically conducted as a melt or as a solution or suspension, preferably as a solution, in a suitable solvent or diluent (see above), in the liquid phase including hydrogen and aminating agent (ammonia or amine), over the catalyst, which is preferably disposed in a heated (preferably externally heated) fixed bed reactor. Both a trickle mode and a liquid phase mode are possible. The catalyst hourly space velocity is generally in the range from 0.05 to 5 kg, preferably from 0.1 to 2 kg, more preferably from 0.2 to 0.6 kg, of sugar alcohol per liter of catalyst (bed volume) and hour.

It is also possible to employ a continuous suspension mode, as described, for example, in EP-A2-1 318 128 (BASF AG) or in FR-A-2 603 276 (Inst. Français du Pétrole).

In the case of performance of the process in the liquid phase, the pressure is generally from 1 to 40 MPa (10-400 bar), preferably from 1.5 to 35 MPa, more preferably from 5 to 30 MPa.

The temperature is generally from 100 to 400° C., preferably from 150 to 300° C., more preferably from 180 to 250° C.

It is appropriate to heat the reactants actually before they are fed into the reaction vessel, preferably to the reaction temperature.

The aminating agent is used preferably in from 0.90 to 250 times the molar amount, preferably in from 1.0 to 100 times the molar amount, especially in from 1.0 to 10 times the molar amount, based in each case on the sugar alcohol.

Especially ammonia is used generally with a 1.5- to 250-fold, preferably from 2- to 100-fold, especially from 2- to 10-fold molar excess per mole of sugar alcohol. Higher excesses both of ammonia and of primary or secondary amines are possible.

The hydrogen is fed to the reaction generally in an amount of from 5 to 400 l, preferably in an amount of from 150 to 600 l, per mole of sugar alcohol, the liter data each having been converted to standard conditions (S.T.P.).

In the case of performance of the process in the liquid phase, the employment of higher temperatures and higher overall pressures is possible. The pressure in the reaction vessel, which arises from the sum of the partial pressures of the aminating agent, of the sugar alcohol and of the reaction products formed and, if appropriate, of the solvent used at the given temperatures, is appropriately raised to the desired reaction pressure by injecting hydrogen.

Both in the case of continuous performance of the process in the liquid phase and in the case of continuous performance of the process in the gas phase, the excess aminating agent can be circulated together with the hydrogen.

When the catalyst is arranged as a fixed bed, it may be advantageous for the selectivity of the reaction to mix the shaped catalyst bodies in the reactor with inert random packings, in effect to "dilute" them. The proportion of the random packings in such catalyst preparations may be from 20 to 80, particularly from 30 to 60 and especially from 40 to 50 parts by volume.

The water of reaction formed in the course of the reaction (in each case one mole per mole of alcohol group converted) generally does not have a disruptive effect on the degree of conversion, the reaction rate, the selectivity and the catalyst lifetime and is therefore appropriately not removed from the reaction product until it is worked up, for example by distillation or extraction.

Typically, the aminating agent is added at the start of the reaction together with sugar alcohols and hydrogen. In a preferred embodiment, it is also possible not to add the aminating agent to the reaction mixture until a portion of the sugar alcohols has been reacted with hydrogen in the presence of one of the catalysts listed above. In this preferred embodiment of the process is generally performed in two stages. In the first stage, the sugar alcohols are typically first converted in the presence of hydrogen and one or more of the catalysts listed above under the reaction conditions specified above. In the second reaction stage, aminating agent is typically added to the reaction mixture from the first stage in the amounts (molar ratios) specified above. In the second reaction stage, the same catalyst can be used as was also used in the first reaction stage, but it is also possible to use another of the catalysts listed above. It is also possible in each case to subdivide the first and/or the second stage into further sub-stages, in which case the same catalyst or another of the catalysts listed above can be used in each sub-stage. It is possible to feed in the aminating agent at the start of the second stage or to divide the supply of the aminating agent between several sub-stages of the second stage.

The multistage reaction of sugar alcohols with hydrogen and aminating agent in the presence of catalysts can be effected batchwise, semicontinuously or continuously.

In the case of continuous performance, the reaction stages or sub-stages are preferably performed in separate reaction chambers, preferably in fixed bed reactors. In the first reaction stage, the reaction of the sugar alcohols with hydrogen is first typically effected in the presence of one of the catalysts listed above. The first stage is preferably performed in a fixed bed reactor, in which case the aminating agent is preferably metered in at the entrance to the second fixed bed reactor.

In the batchwise reaction, the reaction stages can be performed in one or more reactors.

For example, the reaction of sugar alcohol with hydrogen in the presence of a catalyst can first be effected in one reactor and, once a portion of the sugar alcohol has been converted, the aminating agent can then be added to the same reactor. Typically, in this embodiment, the same catalyst is used in the second stage as was also used in the first stage. The aminating agent can be added semicontinuously to the second stage. It is also possible to perform the batchwise two-stage procedure in two reactors, for example two stirred tanks or stirred autoclaves. In the first reactor, the reaction of hydrogen and sugar alcohol is generally first performed in the presence of a catalyst. Once a portion of the sugar alcohol has been converted, the reaction mixture is typically passed into the second reactor, in which the addition of the aminating agent is effected. The catalyst which was used in the first reactor is typically removed from the reaction mixture before it is introduced into the second reactor, for example by filtration. In this variant, a different catalyst is typically used in the first reactor than in the second reactor.

The process according to the invention can prepare amines from sugar alcohols, hydrogen and an amine selected from the group of ammonia and primary and secondary amine.

In general, an amine mixture comprising one or more monoamines selected from the group consisting of methylamine, ethylamine, isopropylamine and n-propylamine, and/or one or more diamines selected from the group consisting of ethylenediamine, 1,2-propanediamine and 1,3-propanediamine, 1,2-butanediamine, 1,3-butanediamine, 1,4-butanediamine and/or one or more alkanolamines selected from the group consisting of monoethanolamine, 2-aminopropan-1-ol and 1-aminopropan-2-ol, and/or one or more sugar alcohol-like specialty amines selected from the group consisting of 1,2,3-triaminopropane, 1,3-diaminopropan-2-ol, 1,2-diaminopropan-3-ol, 1-aminopropanediol, 2-aminopropanediol, glucosamine and isomaltine and/or piperazine, and/or one or more piperazine derivatives selected from the group consisting of 2-methylpiperazine, 2,6-dimethylpiperazine, 2,5-dimethylpiperazine, 2,5-bis(aminomethyl)piperazine, 2,6-bis(aminomethyl)piperazine, 2-aminomethyl-5-methylpiperazine and 2-aminomethyl-6-methylpiperazine is obtained.

Specialty amines are amines which have at least 3 functional groups, at least one functional group being an amine function, for example a primary amino group, a secondary amino group or a tertiary amino group. Specialty amines derive structurally from sugar alcohols or cleavage products thereof, for example 1,2-diaminopropan-3-ol, glucosamine, isomaltine or other sugar alcohols in which one or more hydroxyl groups have been substituted by one amino group.

The composition of the reaction effluent may be influenced by the sugar alcohol conversion, the reaction temperature and the composition of the catalyst.

For example, the composition of the catalyst used may influence the composition of the amines in the reaction effluent.

In a particular embodiment of the process according to the invention, the catalyst used is a catalyst which comprises Ni and/or Co, for example a Raney nickel or cobalt catalyst, or a catalyst which has been obtained by reducing a catalyst precursor and whose active composition, before the reduction with hydrogen, comprises NiO and/or CoO as the catalytic active component. Such catalysts generally have a high activity and especially promote the formation of alkanolamines, diamines, specialty amines and/or piperazine derivatives.

In the case of catalysts which are prepared by reducing catalyst precursors, the presence of the catalytically active component NiO and/or CoO especially promotes the formation of specialty amines and/or piperazine or piperazine derivatives.

In a further preferred embodiment, Raney sponge catalysts with Ni or Co as the active metal are used in the process according to the invention. Raney sponge catalysts with Ni or Co as the active metal generally promote the formation of acyclic diamines or specialty amines. Since these catalysts have a particularly high activity, a high sugar alcohol conversion is generally achieved even at low temperatures or short reaction times a high yield of specialty amines or industrially important amines such as propanediamine and ethylenediamine obtained in the case of use of ammonia as the aminating agent.

In a likewise preferred embodiment, catalysts which comprise one metal or a plurality of metals of the 5th period of groups 8 and/or 9 and/or 10 and/or 11 of the Periodic Table of the Elements, preferably Ru and/or Rh, are used in the process according to the invention. The use of such catalysts generally leads preferentially to the formation of monoamines such as methylamine, ethylamine and/or isopropylamine in the case of use of ammonia as the aminating agent. In particular, catalyst precursors based on Ru, for example as $RuO(OH)_x$, have a high activity.

Preference is also given to an embodiment in which the catalyst used is a Cu catalyst. The use of Cu catalysts leads typically to a relatively high proportion of piperazine derivatives and/or diamines in the reaction effluent.

A further preferred embodiment relates to the use of catalysts which comprise Ir in the process according to the invention. Catalysts which comprise Ir lead generally to a relatively high proportion of specialty amines.

It is also possible to influence the composition of the reaction effluent through the reaction temperature.

For example, in the case of equal conversion at a relatively low reaction temperature, the formation of specialty amines and acyclic amines, such as diamines and alkanolamines, is generally promoted.

When the reaction is performed at a relatively high reaction temperature up to the same conversion, generally piperazine or piperazine derivatives are formed by cyclization reactions. At a relatively high reaction temperature, deamination reactions generally increase with the same conversion; for example, piperazine is formed from aminomethylpiperazine, or monoethylamine is formed from ethylenediamine.

The composition of the reaction effluent can also be influenced through the sugar alcohol conversion.

For instance, it is observed that the number of functionalities generally decreases (defunctionalization) in the case of high conversions, irrespective of the catalyst used, i.e., for example, di- or monoamines are formed from triamines, or methylpiperazines from aminomethylpiperazines.

Moreover, in the case of high sugar alcohol conversions, an increase in the cyclization and, associated with this, the formation of piperazine or piperazine derivatives is observed.

High sugar alcohol conversions, for example sugar alcohol conversions of 80% and more, preferably 90% and more, more preferably 99% and more, generally favor the formation of reaction effluents with a high proportion of cyclic amines, such as piperazine and/or piperazine derivatives.

Moderate sugar alcohol conversions, for example sugar alcohol conversions of from 30 to 80%, preferably from 40 to 70% and more preferably from 50 to 60%, generally promote the formation of specialty amines.

The sugar alcohol conversion can be influenced by a series of process parameters, such as pressure, temperature, the molar ratio of aminating agent, especially ammonia, to sugar alcohol, and the reaction or residence time.

The sugar alcohol conversion ($C_{sugar\ alcohol}$) can be determined as a matter of routine by gas chromatography analysis by the person skilled in the art and is typically reported as follows:

$$C_{sugar\ alcohol} = (A\%_{sugar\ alcohol,start} - A_{sugar\ alcohol,end})/A_{sugar\ alcohol,start};$$

where $A\%_{sugar\ alcohol,\ start}$ and A % sugar alcohol, end are the area percentages, determined by means of gas chromatography, below the sugar alcohol signal which was measured at the start and end of the reaction or at the input or output of the reactor.

High sugar alcohol conversions, for example from 80 to 100%, can be achieved, for example, by an increase in the temperature or an increase in the molar ratio of aminating agent, especially ammonia, to sugar alcohol.

For example, high sugar alcohol conversions can be achieved within a temperature range of generally from 200 to 400° C., preferably from 220 to 350° C.

Typically, the molar ratio of aminating agent, especially of ammonia, to sugar alcohol to achieve high sugar alcohol conversions is in the range from 5:1 to 250:1, preferably from 10:1 to 150:1.

In a continuous process, it is possible to bring about a relatively high sugar alcohol conversion by a reduction in the catalyst hourly space velocity.

High sugar alcohol conversions are achieved generally at catalyst hourly space velocities in the range from 0.05 to 0.6 kg of sugar alcohol per liter of catalyst (bed volume) and hour, preferably from 0.05 to 0.2 per liter of catalyst (bed volume) and hour.

It is additionally possible to bring about a high sugar alcohol conversion in a batchwise process by an increase in the residence time or by an increase in the catalyst concentration. Typically, high sugar alcohol conversions are achieved at residence times of from 16 to 72 hours, preferably from 20 to 48 hours and more preferably from 24 to 32 hours, where the residence time may also be shorter or longer depending on the catalyst concentration in order to achieve a high sugar alcohol conversion.

Moderate sugar alcohol conversions, for example from 30 to 80%, can be achieved, for example, by a reduction in the temperature or a reduction in the molar ratio of ammonia to sugar alcohol.

Moderate sugar alcohol conversions may be achieved, for example, within a temperature range of generally from 150 to 300° C., preferably from 150 to 220° C. Typically, the molar ratio of aminating agent, especially ammonia, to sugar alcohol in the case of achievement of high conversions is in the range from 1:1 to 100:1, preferably from 2.5:1 to 50:1.

It is possible to bring about a reduction in the sugar alcohol conversion in a continuous process by an increase in the catalyst hourly space velocity. Moderate sugar alcohol conversions are generally achieved at catalyst hourly space velocities in the range from 0.1 to 1.2 kg of sugar alcohol per liter of catalyst (bed volume) and hour, preferably from 0.2 to 0.6 per liter of catalyst (bed volume) and hour.

In a batchwise process, it is possible to reduce the sugar alcohol conversion by a shortening of the residence time or by a reduction in the catalyst concentration. Moderate sugar alcohol conversions are generally achieved in the case of residence times of from 5 to 20 hours, preferably from 10 to 16 hours, where the residence time may also be shorter or longer depending on the catalyst concentration in order to achieve a moderate sugar alcohol conversion.

In a particularly preferred embodiment, a catalyst comprising Ni and/or Co is used and a moderate sugar alcohol conversion, for example a sugar alcohol conversion of from 30 to 80%, preferably from 40 to 70% and more preferably from 50 to 60%, is established.

A moderate sugar alcohol conversion can typically be established as described above. In the case of a moderate sugar alcohol conversion and the use of nickel and/or cobalt catalysts, a high proportion of specialty amines is generally formed with preference. The reaction effluent obtained through this particular embodiment of the process comprises a proportion of specialty amines of generally more than 5% by weight, preferably more than 10% by weight, based on the total mass of the amines formed.

In a further preferred embodiment, an Ir catalyst is used and a moderate sugar alcohol conversion is established.

The establishment of a moderate sugar alcohol conversion, for example from 30 to 80%, can generally be achieved in the manner detailed above.

The reaction effluent obtained through this particular embodiment of the process comprises a proportion of specialty amines of generally more than 5% by weight, preferably more than 10% by weight, based on the total mass of the amines formed.

In a further preferred embodiment, in the case of use of a catalyst comprising Ni and/or Co, a high sugar alcohol conversion, for example more than 80%, preferably more than 90%, more preferably more than 99%, is established.

High sugar alcohol conversions may, for example, be established as described above. The reaction effluent obtained through this particular embodiment of the process comprises a proportion of piperazine and/or piperazine derivatives of generally more than 10% by weight, preferably from 20% by weight to 80% by weight and more preferably from 30 to 70% by weight, based on the total mass of the amines formed.

In a further preferred embodiment, a catalyst which comprises one metal or a plurality of metals of the 5th period of groups 8 and/or 9 and/or 10 and/or 11 is used and a high sugar alcohol conversion is established.

The establishment of a high sugar alcohol conversion, for example more than 80%, can generally be achieved in the manner detailed above.

The reaction effluent obtained through this specific embodiment of the process comprises a proportion of monoamines of generally more than 10% by weight, based on the total mass of the amines formed.

In a very particularly preferred embodiment, an Ni and/or Co catalyst is used within a temperature range from 150 to 220° C. In this preferred embodiment, a high sugar alcohol conversion, for example more than 80%, preferably more than 90%, more preferably more than 99%, is established, for example by reducing the catalyst hourly space velocity or increasing the residence time. The very particular embodiment differs from the aforementioned embodiment using Ni and/or Co catalysts with a high sugar alcohol conversion in that a high sugar alcohol conversion is established at temperatures in the range of 150 and 220° C. instead of from 220 to 350° C.

In the continuous variant of this very particular embodiment, the catalyst hourly space velocity is generally in the range from 0.05 to 0.6 kg of sugar alcohol per liter of catalyst (bed volume) and hour, preferably from 0.05 to 0.2 per liter of catalyst (bed volume) and hour.

In the batchwise variant of this very particular embodiment, a high sugar alcohol conversion can generally be achieved by prolonging the residence time or by increasing the catalyst concentration. Typically, the residence time in this particularly preferred embodiment is a residence time of more than 20 hours, preferably more than 24 hours and more preferably more than 30 hours, where the residence time may also be shorter or longer depending on the catalyst concentration.

Typically, the molar ratio of aminating agent, especially of ammonia, to sugar alcohol to achieve high sugar alcohol conversions in this very particular embodiment is in the range from 5:1 to 250:1, preferably from 10:1 to 150:1.

The reaction effluent obtained by this very particular embodiment of the process comprises a proportion of diaminopropane, diaminopropanol and triaminopropane of more than 10% by weight, preferably from 15% by weight to 80% by weight and more preferably from 20 to 70% by weight, based on the total mass of the amines.

The reaction effluent generally comprises the amines prepared in accordance with the invention, and also water, aminating agent, hydrogen and any unconverted sugar alcohol.

The excess aminating agent and the hydrogen are removed from the reaction effluent once it has appropriately been decompressed. The excess aminating agent and the hydrogen are advantageously recycled back into the reaction zone.

After the aminating agent and the hydrogen have been removed, the reaction effluent thus obtained is generally worked up.

In general, the reaction effluent is dewatered, since water and amines can form azeotropes which can complicate the distillative separation of the individual amines of the reaction effluent.

The aqueous reaction effluent is dewatered typically by contacting the aqueous reaction effluent with sodium hydroxide solution.

The concentration of the sodium hydroxide solution is typically from 20 to 80%, preferably from 30 to 70% and more preferably from 40 to 60%.

The volume ratio of sodium hydroxide solution added and the reaction effluent is typically between 0.5:1 to 2:1, preferably 1:1.

The reaction effluent can be contacted with sodium hydroxide solution by supplying the sodium hydroxide solution to the reaction reactor in which the hydrogenating amination of sugar alcohol has been performed beforehand. In the case of a continuous reaction, the sodium hydroxide solution can be metered in as a continuous stream at the reactor outlet. However, it can also be contacted with the vaporous reaction effluent in the manner of an extractive distillation in a distillation column in countercurrent. Processes for extractive distillation are described, for example, in GB-A-1,102,370 or EP-A-1312600.

In a preferred variant, the reaction effluent is dewatered, for example, when a moderate sugar alcohol conversion is established, since sugar alcohol can, in general, typically be removed from the amines formed together with the aqueous phase completely or at least virtually completely.

The reaction effluent can be separated by distillation or rectification, liquid extraction or crystallization, in which case the separation can be effected in one or more stages, the number of stages generally being dependent on the number of components present in the reaction effluent.

The reaction effluent can be separated into fractions which comprise a mixture of different amine components, or into fractions which comprise only one amine component.

For example, a separation can first be effected into fractions which comprise more than one amine component. These fractions can subsequently be separated into the individual compounds or components, for example by a fine distillation.

Unconverted sugar alcohol can be recycled into the process.

The fractions obtained in the workup of the reaction effluent, comprising one or more amines, may be used, for example, as additives in concrete and/or cement production.

Such fractions comprise, for example:
from 0 to 5% by weight of diamines such as 1,2-diaminopropane;
from 5 to 20% by weight of piperazine derivatives such as 2-methylpiperazine, 2,5-bis-(aminomethyl)piperazine, 3,5-bis(aminomethyl)piperazine, 2-aminomethyl-6-methyl-piperazine, 3-aminomethyl-5-methylpiperazine and/or 3-aminomethyl-6-methyl-piperazine;
from 10 to 30% by weight of specialty amines such as 1,2,3-triaminopropane, 1,2-diaminopropan-3-ol and/or 1,3-diaminopropan-2-ol and
from 20 to 45% by weight of sugar alcohol.

In addition, such a fraction may comprise from 15 to 30% by weight of water and further components such as monoamines, diamines, piperazine, piperazine derivatives and/or alkanolamines.

The amines obtained in accordance with the invention, such as monoamines selected from the group consisting of methylamine, ethylamine, isopropylamine and n-propylamine, and/or one or more diamines selected from the group consisting of ethylenediamine, 1,2-propanediamine and 1,3-propanediamine, 1,2-butanediamine, 1,3-butanediamine, 1,4-butanediamine and/or one or more alkanolamines selected from the group consisting of monoethanolamine, 2-aminopropan-1-ol and 1-aminopropan-2-ol, and/or one or more sugar alcohol-like specialty amines selected from the group consisting of 1,2,3-triaminopropane, 1,3-diaminopropan-2-ol, 1,2-diaminopropan-3-ol, 1-aminopropanediol, 2-aminopropanediol, glucosamine and isomaltine and/or piperazine, and/or one or more piperazine derivatives selected from the group consisting of 2-methylpiperazine, 2,6-dimethylpiperazine, 2,5-dimethylpiperazine, 2,5-bis(aminomethyl)piperazine, 2,6-bis(aminomethyl)piperazine, 2-aminomethyl-5-methylpiperazine and 2-aminomethyl-6-methylpiperazine can be used as a synthesis unit for the production of surfactants, medicaments and crop protection compositions, stabilizers including light stabilizers, polymers, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

The advantages of the present invention consist in the fact that sugar alcohol is used effectively as a source for the preparation of amines. A process is provided which allows both important industrial amines to be obtained, and also specialty amines and piperazine derivatives, in order to utilize the sugar alcohol raw material optimally.

The conversion of sugar alcohol includes only a few reaction steps.

By virtue of simple-to-perform adjustments to the process conditions, for example pressure and temperature, and also by virtue of the selection of the catalyst, it is possible to regulate the composition of the reaction effluent within certain limits in order to be able to react flexibly to variations in demand and sales.

By virtue of this process, it is possible to obtain important industrial amines, for example monoamines such as methylamine, ethylamine, isopropylamine or n-propylamine, diamines such as ethylenediamine, 1,2-propanediamine or 1,3-propanediamine, alkanolamines such as monoethanolamine, 2-aminopropan-1-ol or 1-aminopropan-2-ol, or piperazine, which have to date been prepared from petrochemical starting materials. However, novel specialty amines are also obtained. These compounds display a high number of functionalities and may therefore constitute important intermediates in the synthesis of organic compounds, such as crop protection compositions, pharmaceuticals, stabilizers, etc.

Moreover, derivatives of piperazine (piperazine derivatives) such as 2-methylpiperazine, 2,6-dimethylpiperazine, 2,5-dimethylpiperazine, 2,5-bis-(aminomethyl)piperazine, 2,6-bis(aminomethyl)piperazine, 2-aminomethyl-5-methylpiperazine or 2-aminomethyl-6-methylpiperazine, are also obtained, which may likewise constitute important synthesis units.

The tendency to form aromatic by-products, especially pyrazines and pyrazine derivatives, is low in the process according to the invention.

The process according to the invention is explained with reference to the examples which follow.

EXAMPLES 1 TO 2 AND COMPARATIVE EXAMPLES 1 TO 3

General Procedure:

A high-pressure autoclave was charged with 5 g of pulverulent catalyst and 15 g of substrate dissolved in 22.5 g of water. The reactor was inertized and 90 g of ammonia were added. The inert gas was exchanged for hydrogen and then hydrogen was injected to a pressure of 20 bar. The reactor was heated to 100° C. and the hydrogen pressure was increased to 50 bar on attainment of the temperature. The reaction mixture was stirred at 100° C. and 50 bar for 1 hour. Subsequently, the temperature was increased continuously to 200° C. within 2 hours and the reaction mixture was stirred for 1 hour after the 200° C. had been attained. Subsequently, the pressure was increased to 200 bar by injecting hydrogen. The pressure was kept constant at this value over the entire duration of the reaction. After a reaction time of 32 hours, a sample was taken and analyzed. The contents of the compounds were determined by means of gas chromatography (conditions: RTX 5 Amine 30 m capillary column, film thickness 1.5 micrometers, diameter 0.32 mm, method: 60° C. at 5 min, then heat to 280° C. at 7° C./min and continue heating at 280° C. for 20 min) as area percentages (A %). In this context, the area percentages of the signals relate to the total area below the signals measured with the exception of the water signal.

The sugar alcohol conversions reported are based on the area percentages determined before the start and at the end of the reaction.

Example 1

The preparation was effected as described in the general procedure. The substrate used was sorbitol. The catalyst used was a Raney nickel catalyst. The end temperature was 200° C.

The gas chromatography analysis after 32 hours gave the following composition:
ethylenediamine: 8%; 1,2-propylenediamine: 12%; piperazine: 4%; 2-methylpiperazine: 12%; 2,6-dimethylpiperazine: 0%; 2,5-dimethylpiperazine: 4%; heteroaromatics: 6%. The sorbitol conversion was approx. 100%.

Example 2

The preparation was effected as described in the general procedure. The substrate used was sorbitol. The catalyst used was a catalyst which had been obtained by prereduction from a catalyst precursor whose catalytically active composition, before the reduction with hydrogen, comprised 13% by weight of Cu, calculated as CuO, 28% by weight of Ni, calculated as NiO, 28% by weight of Co, calculated as CoO, and 31% by weight of Zr, calculated as $ZrO_2$. The end temperature was 200° C.

The gas chromatography analysis after 32 hours gave the following composition:
ethylenediamine: 8%; 1,2-propylenediamine: 17%; piperazine: 11%; 2-methylpiperazine: 25%; 2,6-dimethylpiperazine: 8%; 2,5-dimethylpiperazine: 6%; heteroaromatics: 0%. The sorbitol conversion was approx. 100%.

Comparative Example 1

The preparation was effected as described in the general procedure. The substrate used was glucose. The catalyst used was a Raney nickel catalyst. The end temperature was 200° C.

The gas chromatography analysis after 32 hours gave the following composition:
ethylenediamine: 15%; 1,2-propylenediamine: 13%; piperazine: 3%; 2-methylpiperazine: 12%; 2,6-dimethylpiperazine: 1%; 2,5-dimethylpiperazine: 7%; heteroaromatics: 11%. The glucose conversion was approx. 100%.

Comparative Example 2

The preparation was effected as described in the general procedure. The substrate used was glucose. The catalyst used was a catalyst which had been obtained by prereduction from a catalyst precursor whose catalytically active composition, before the reduction with hydrogen, comprised 13% by weight of Cu, calculated as CuO, 28% by weight of Ni, calculated as NiO, 28% by weight of Co, calculated as CoO, and 31% by weight of Zr, calculated as $ZrO_2$. The end temperature was 200° C.

The gas chromatography analysis after 32 hours gave the following composition:
ethylenediamine: 7%; 1,2-propylenediamine: 15%; piperazine: 3%; 2-methylpiperazine: 9%; 2,6-dimethylpiperazine: 0%; 2,5-dimethylpiperazine: 1%; heteroaromatics: 14%. The glucose conversion was approx. 100%.

Comparative Example 3

The preparation was effected as described in the general procedure. The substrate used was sucrose. The catalyst used was a Raney nickel catalyst. The end temperature was 200° C.

The gas chromatography analysis after 32 hours gave the following composition:
ethylenediamine: 6%; 1,2-propylenediamine: 5%; piperazine: 8%; 2-methylpiperazine: 20%; 2,6-dimethylpiperazine: 2%; 2,5-dimethylpiperazine: 0%; heteroaromatics: 21%. The sucrose conversion was approx. 100%.

Example 3

A high-pressure autoclave was charged with 21 g of catalyst, 15 g of sorbitol dissolved in 61.5 g of water and 0.75 g of calcium oxide. The catalyst used was a mixture of a palladium catalyst which was supported on activated carbon and had a Pd content of approx. 5% by weight and water, and the water content of the mixture was 64%.

The reactor was inertized. The inert gas was exchanged for hydrogen and then hydrogen was injected to a pressure of 100 bar. The reactor was heated to an end temperature of 230° C., and the hydrogen pressure was increased to 250 bar. After 10 hours, the reactor was cooled to room temperature and decompressed slowly.

The reactor contents were filtered off from the catalyst and charged again into a high-pressure autoclave. 5 g of reduced catalyst were added. The catalyst used was a catalyst which had been obtained by prereduction from a catalyst precursor whose catalytically active composition before the reduction with hydrogen comprised 13% by weight of Cu, calculated as CuO, 28% by weight of Ni, calculated as NiO, 28% by weight of Co, calculated as CoO, and 31% by weight of Zr, calculated as $ZrO_2$. The reactor was inertized and 55 g of ammonia were added, and hydrogen was injected to a pressure of 20 bar. The reactor was heated to 100° C. and the hydrogen pressure, on attainment of the temperature, was increased to 50 bar. The reaction mixture was stirred at 100° C. and 50 bar for 1 hour. Subsequently, the temperature was increased continuously to 190° C. within 2 hours and the reaction mixture was stirred for 1 hour on attainment of the 190° C. Subsequently, the pressure was increased to 200 bar by injecting hydrogen. The pressure was kept constant at this value over the entire duration of the reaction. After a reaction time of 32 hours, a sample was taken and analyzed. The contents of the compounds were determined by means of gas chromatography (conditions: RTX 5 Amine 30 m capillary column, film thickness 1.5 micrometers, diameter 0.32 mm, method: 5 min. at 60° C., then heat to 280° C. at 7° C./min and continue heating at 280° C. for 20 min) as area percentages (A %). In this context, the area percentages of the signals are based on the total area below the signals measured with the exception of the water signal. The sugar alcohol conversions reported are based on the area percentages determined before the start and at the end of the reaction.

The gas chromatography analysis after 32 hours gave rise to the following composition:
ethylenediamine: 9%; 1,2-propylenediamine: 28%; piperazine: 6%; 2-methylpiperazine: 17%; 2,6-dimethylpiperazine: 11%; 2,5-dimethylpiperazine: 3%; heteroaromatics: 0%. The sorbitol conversion was approx. 100%.

Example 4

The preparation was effected as described in the general procedure analogously to example 1. However, 75 g of water and only 55 g of ammonia were used. The substrate used was sorbitol. The catalyst used was a catalyst which had been obtained by prereduction from a catalyst precursor whose catalytically active composition before the reduction with hydrogen comprised 13% by weight of Cu, calculated as CuO, 28% by weight of Ni, calculated as NiO, 28% by weight of Co, calculated as CoO, and 31% by weight of Zr, calculated as $ZrO_2$. The end temperature was 190° C.

The gas chromatography analysis after 32 hours gave rise to the following composition:
ethylenediamine: 6%; 1,2-propylenediamine: 13%; piperazine: 4%; 2-methylpiperazine: 18%; 2,6-dimethylpiperazine: 12%; 2,5-dimethylpiperazine: 4%; heteroaromatics: 0%. The sorbitol conversion was approx. 100%.

EXAMPLES 5 TO 10

General Procedure:

A high-pressure autoclave was initially charged with 0.5 g of pulverulent catalyst, 4.8 g of sorbitol and 6.5 g of water. The reactor was inertized and ammonia was added. The inert gas was exchanged for hydrogen and then hydrogen was injected to a pressure of 50 bar. With stirring, the reactor was heated to 200° C. within 2 hours and, on attainment of this temperature, the pressure was increased to 200 bar by injecting hydrogen. The pressure was kept constant at this value over the entire duration of the reaction. After a reaction time of 24 hours, the reactor was cooled to RT and decompressed slowly at room temperature. The degassed reactor contents were analyzed. The contents of the compounds determined by means of gas chromatography (conditions: RTX 5 Amine 30 m capillary column, film thickness 1.5 micrometers, diameter 0.32 mm, method: 60° C. for 5 min, then heat to 280° C. at 7° C./min and continue heating at 280° C. for 20 min) as area percentages (A %). In this context, the area percentages of the signals are based on the total area below the signals measured with the exception of the water signal. The sugar alcohol conversions reported are based on the area percentages determined before the start and at the end of the reaction.

Example 5

The preparation was effected as described in the general procedure. The catalyst used was a catalyst which had been obtained by prereduction from a catalyst precursor whose catalytically active composition before the reduction with hydrogen comprised 13% by weight of Cu, calculated as CuO, 28% by weight of Ni, calculated as NiO, 28% by weight of Co, calculated as CoO, and 31% by weight of Zr, calculated as $ZrO_2$. The catalyst precursor was prereduced at a temperature of 280° C. under a pure hydrogen atmosphere for 20 hours.

The gas chromatography analysis showed the following composition:
ethylenediamine: 1%; monoethanolamine: 1%, monoethylene glycol: 2%, 1,2-propanediamine: 2%, 2-aminopropan-1-ol: 4%; 2-methylpiperazine: 2%; 2,6-dimethylpiperazine: 3%; 2,5-dimethylpiperazine: 3%; $C_4$ diamines (1,2-butanediamine, 1,3-butanediamine, 1,4-butanediamine): 3%; heteroaromatics: 0%; sorbitol: 36%. The sorbitol conversion was approx. 64%.

Example 6

The preparation was effected as described in the general procedure. The catalyst used was a catalyst which was obtained by prereduction from a catalyst precursor whose catalytically active composition consisted of $LiCoO_2$. The catalyst precursor was prereduced at a temperature of 300° C. under a pure hydrogen atmosphere for 20 hours.

The gas chromatography analysis showed the following composition:
ethylenediamine: 0%; monoethanolamine: 4%, monoethylene glycol: 0%, 1,2-propanediamine: 0%, 2-aminopropan-1-ol: 5%; 2-methylpiperazine: 3%; 2,6-dimethylpiperazine: 3%; 2,5-dimethylpiperazine: 2%; $C_4$ diamines (1,2-butanediamine, 1,3-butanediamine, 1,4-butanediamine): 8%; heteroaromatics: 1%; sorbitol: 22%. The sorbitol conversion was approx. 78%.

Example 7

The preparation was effected as described in the general procedure. The catalyst used was a catalyst which was obtained by prereduction from a catalyst precursor whose catalytically active composition consisted of $RuO(OH)_x$.

The gas chromatography analysis showed the following composition:
ethylamine: 2%; propylamine: 2%; ethylenediamine: 0%; monoethanolamine: 0%, monoethylene glycol: 1%, 1,2-propanediamine: 0%, 2-aminopropan-1-ol: 0%; 2-methylpiperazine: 0%; 2,6-dimethylpiperazine: 0%; 2,5-dimethylpiperazine: 2%; $C_4$ diamines (1,2-butanediamine, 1,3-butanediamine, 1,4-butanediamine): 0%; heteroaromatics: 0%; sorbitol: 13%.
The sorbitol conversion was approx. 87%.

Example 8

The preparation was effected as described in the general procedure. The catalyst used was a catalyst which was obtained by prereduction from a catalyst precursor whose catalytically active composition before reduction with hydrogen comprised 85% by weight of Co, calculated as CoO, and 5% by weight of Mn, calculated as $Mn_3O_4$. The catalyst precursor was prereduced at a temperature of 280° C. under a pure hydrogen atmosphere for 12 hours.

The gas chromatography analysis showed the following composition:
ethylenediamine: 1%; monoethanolamine: 0%, monoethylene glycol: 0%, 1,2-propanediamine: 0%, 2-aminopropan-1-ol: 1%; 2-methylpiperazine: 0%; 2,6-dimethylpiperazine: 0%; 2,5-dimethylpiperazine: 0%; $C_4$ diamines (1,2-butanediamine, 1,3-butanediamine, 1,4-butanediamine): 0%; heteroaromatics: 0%; sorbitol: 71%. The sorbitol conversion was approx. 29%.

Example 9

The preparation was effected as described in the general procedure. The catalyst used was a catalyst which had been obtained by prereduction from a catalyst precursor whose catalytically active composition before reduction with hydrogen comprised 76% by weight of Co, calculated as CoO, 23% by weight of Cu, calculated as CuO, 9% by weight of Mn, calculated as $MnO_2$, 4% by weight of Mo, calculated as $MoO_3$, 2.7% by weight of P, calculated as $P_2O_5$, and 0.2% by weight of Na, calculated as $Na_2O$. The catalyst precursor was prereduced at a temperature of 280° C. under a pure hydrogen atmosphere for 20 hours.

The gas chromatography analysis showed the following composition:
ethylenediamine: 0%; monoethanolamine: 0%, monoethylene glycol: 0%, 1,2-propanediamine: 1%, 2-aminopropan-1-ol: 3%; 2-methylpiperazine: 1%; 2,6-dimethylpiperazine: 1%; 2,5-dimethylpiperazine: 1%; $O_4$ diamines (1,2-butanediamine, 1,3-butanediamine, 1,4-butanediamine): 2%; heteroaromatics: 0%; sorbitol: 58%. The sorbitol conversion was approx. 42%.

Example 10

Corresponds to Example 12 Sorbitol, Raney Co

The preparation was effected as described in the general procedure. The catalyst used was Raney cobalt (Raney® 2724 from Grace Davison).

The gas chromatography analysis showed the following composition:

ethylenediamine: 0%; monoethanolamine: 2%, monoethylene glycol: 0%, 1,2-propanediamine: 0%, 2-aminopropan-1-ol: 2%; 2-methylpiperazine: 1%; 2,6-dimethylpiperazine: 0%; 2,5-dimethylpiperazine: 1%; $C_4$ diamines (1,2-butanediamine, 1,3-butanediamine, 1,4-butanediamine): 4%; heteroaromatics: 0%; sorbitol: 35%. The sorbitol conversion was approx. 65%.

The invention claimed is:

1. A process for preparing amines which comprises reacting sorbitol with hydrogen and an aminating agent selected from the group of ammonia, methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine, and pyrrolidine in the presence of a catalyst at a temperature of from 100° C. to 400° C. and a pressure of from 1 to 40 MPa, wherein a reaction effluent is obtained which comprises
one or more monoamines selected from the group consisting of methylamine, ethylamine, isopropylamine and n-propylamine, and/or one or more diamines selected from the group consisting of ethylenediamine, 1,2-propanediamine and 1,3-propanediamine, 1,2-butanediamine, 1,3-butanediamine, 1,4-butanediamine and/or
one or more alkanolamines selected from the group consisting of monoethanolamine, 2-aminopropan-1-ol and 1-aminopropan-2-ol, and/or
one or more sugar alcohol-like specialty amines selected from the group consisting of 1,2,3-triaminopropane, 1,3-diaminopropan-2-ol, 1,2-diaminopropan-3-ol, 1-aminopropanediol, 2-aminopropanediol, glucosamine and isomaltine and/or piperazine, and/or
one or more piperazine derivatives selected from the group consisting of 2-methylpiperazine, 2,6-dimethylpiperazine, 2,5-dimethylpiperazine, 2,5-bis(aminomethyl)piperazine, 2,6-bis(aminomethyl)piperazine, 2-aminomethyl-5-methylpiperazine and 2-aminomethyl-6-methylpiperazine.

2. The process according to claim 1, wherein the sorbitol has been obtained by hydrogenating the corresponding sugars.

3. The process according to claim 1, wherein the catalyst comprises one metal or a plurality of metals or one or more oxygen compounds of the metals of groups 8 and/or 9 and/or 10 and/or 11 of the Periodic Table of the Elements.

4. The process according to claim 3, wherein the catalyst comprises Ni or NiO and/or Co or CoO.

5. The process according to claim 3, wherein the catalyst is a Raney sponge catalyst comprising Ni or Co or a mixture thereof.

6. The process according to claim 3, wherein the catalyst comprises one metal or a plurality of metals of the 5th period of groups 8 and/or 9 and/or 10 and/or 11 of the Periodic Table of the Elements.

7. The process according to claim 3, wherein the catalyst comprises Cu or CuO.

8. The process according to claim 3, wherein the catalyst comprises Ir.

9. The process according to claim 1, wherein the sorbitol conversion is in the range from 30 to 80%.

10. The process according to claim 9, wherein the catalyst hourly space velocity is in the range from 0.1 to 1.2 kg of sorbitol per liter of catalyst per hour, and the temperature is in the range from 150 to 220° C.

11. The process according to claim 1, wherein the sorbitol conversion is in the range from 80 to 100%.

12. The process according to claim 11, wherein the catalyst hourly space velocity is in the range from 0.05 to 0.6 kg of sorbitol per liter of catalyst per hour, and the temperature is in the range from 220 to 350° C.

13. The process according to claim 11, wherein the temperature is in the range from 150 to 220° C.

14. The process according to claim 1, wherein a reaction effluent exiting from the process is worked up by distillation.

15. The process according to claim 14, wherein the reaction effluent is dewatered before the distillative workup.

16. The process according to claim 14, wherein the reaction effluent, after the aminating agent has been removed by distillation, has an aminating agent content of less than 1000 ppm.

17. The process according to claim 1, which is performed in two stages, wherein the sorbitol is first reacted with hydrogen in the presence of a catalyst in the first stage and, once a portion of the sorbitol has been converted, the aminating agent is added to the reaction mixture in a second stage.

18. The process according to claim 1, wherein the aminating agent used is ammonia.

19. A process for preparing amines which comprises reacting sorbitol with hydrogen and ammonia, in the presence of a catalyst at a temperature of from 100° C. to 400° C. and a pressure of from 1 to 40 MPa, wherein the catalyst comprises Ni or NiO, and/or Co or CoO, and/or Cu or CuO, or a Raney sponge including Ni or Co or a mixture thereof, wherein the conversion of sorbitol is from 80% to 100%.

20. The process according to claim 19 wherein the catalyst comprises a mixture of Ni or NiO, Co or CoO, and Cu or CuO, and the temperature is in the range from 150 to 250° C.

21. The process according to claim 20 with a reaction effluent comprising ethylenediamine, 1,2-propylenediamine, 2-methylpiperazine, 2,6-dimethylpiperazine, and 2,5-dimethylpiperzine.

22. The process according to claim 21 wherein the reaction effluent comprises;
12% to 28% by weight 1,2-propylenediamine,
12% to 25% by weight 2-methylpiperazine, and
0% to 6% by weight heteroaromatics, the percent by weight based on a total mass of amines formed.

23. The process according to claim 20 with a reaction effluent comprising 30% to 70% by weight piperazine and piperazine derivatives, the percent by weight based on a total mass of amines formed.

24. The process according to claim 19 wherein the reaction effluent is dewatered with NaOH, the volume ratio of NaOH to the reaction effluent is from 0.5:1 to 2:1.

25. The process according to claim 20 further comprising adding water to the reaction of sorbitol, ammonia and hydrogen.

26. The process according to claim 19 wherein the reaction of sorbitol with hydrogen and ammonia includes reacting the sorbitol with hydrogen in the presence of the catalyst, followed by the addition of the ammonia, also in the presence of the catalyst.

27. A process for preparing amines comprising reacting sorbitol with hydrogen and an aminating agent selected from the group consisting of ammonia, methylamine, dimethylamine, ethylamine, piperidine, morpholine, and pyrrolidine in the presence of a catalyst selected from Ni or NiO and Co or CoO, or a mixture of Ni or NiO, Co or CoO, and Cu or CuO, at a temperature of from 220° C. to 350° C. and a pressure of from 5 to 30 MPa, wherein the conversion of sorbitol is from 30% to 80%.

28. The process according to claim 26 with a reaction effluent comprising diaminopropane, diaminopropanol and triaminopropane, the diaminopropane, the diaminopropanol and the triaminopropane accounting for 15% to 80% by weight, based on the total mass of the amines in the reaction effluent.

\* \* \* \* \*